United States Patent
Sivakumar et al.

(10) Patent No.: US 7,951,961 B2
(45) Date of Patent: May 31, 2011

(54) ENANTIOSELECTIVE SYNTHESIS OF PYRROLIDINES SUBSTITUTED WITH FLAVONES, AND INTERMEDIATES THEREOF

(75) Inventors: Meenakshi Sivakumar, Maharastra (IN); Manoj Shukla, Maharashtra (IN); Pramod Kumar Jadhav, Maharashtra (IN); Ajit Borhade, Maharashtra (IN)

(73) Assignee: Piramal Life Sciences Limited (IN)

( * ) Notice: Subject to any disclaimer, the term of this patent is extended or adjusted under 35 U.S.C. 154(b) by 34 days.

(21) Appl. No.: 12/307,645

(22) PCT Filed: Jul. 7, 2006

(86) PCT No.: PCT/IB2006/052294
§ 371 (c)(1),
(2), (4) Date: Oct. 8, 2009

(87) PCT Pub. No.: WO2008/007169
PCT Pub. Date: Jan. 17, 2008

(65) Prior Publication Data
US 2010/0113803 A1    May 6, 2010

(51) Int. Cl.
*C07D 295/00* (2006.01)
(52) U.S. Cl. .................. 548/570; 548/543; 548/551
(58) Field of Classification Search .............. 548/570, 548/543, 551
See application file for complete search history.

(56) References Cited

U.S. PATENT DOCUMENTS
6,784,167 B2 * 8/2004 Wood et al. .................. 514/63

FOREIGN PATENT DOCUMENTS
WO   WO 2004-004632   1/2004
WO   WO 2007-148158   12/2007

OTHER PUBLICATIONS

Barnes et al., J. Am. Chem. Soc., 2002, 124 (44), 13097-13105.
Ghosh et al., Tetrahedron: Asymmetry, (1998), vol. 9, p. 1-45.
Naik et al., Tetrahedron, vol. 44., No. 7, (1988) p. 2081-2086, Great Britain, XP002093909.

* cited by examiner

*Primary Examiner* — Yong Chu
*Assistant Examiner* — Valerie Rodriguez-Garcia
(74) *Attorney, Agent, or Firm* — Frommer Lawrence & Haug LLP

(57) ABSTRACT

The present invention relates to an enantioselective synthesis of (+)-trans enantiomer of pyrrolidines substituted with flavones, represented by Formula 1 or salts thereof, which are inhibitors of cyclin dependant kinases and can be used for treatment of proliferative disorders such as cancer Formula 1 wherein Ar has the meaning as indicated in the claims.

15 Claims, No Drawings

ENANTIOSELECTIVE SYNTHESIS OF PYRROLIDINES SUBSTITUTED WITH FLAVONES, AND INTERMEDIATES THEREOF

FIELD OF INVENTION

The present invention relates to an enantioselective synthesis of the (+)-trans enantiomer of pyrrolidines substituted with flavones, represented by the compounds of Formula 1 or salts thereof, which are inhibitors of cyclin dependant kinases and can be used for treatment of proliferative disorders such as cancer.

BACKGROUND OF THE INVENTION

Cyclin dependent kinases (Cdks) are essential enzymes for the control of cell cycle progression. Inhibitors of cyclin-dependent kinases are anticipated to possess therapeutic utility against a wide variety of proliferative diseases, especially cancer. As a result of this, the CDKs have been targeted for drug discovery and a number of small molecule inhibitors of CDKs have been identified and studied. Inhibitors of CDK/cyclin complexes represented by the following general Formula 1;

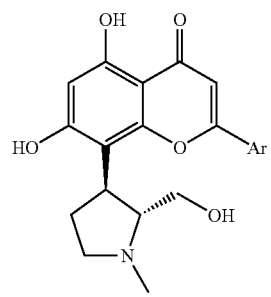

Formula 1 wherein Ar is defined in the detailed description;
have been described in PCT Patent Application No. PCT/IB2006/052002, which is incorporated herein by reference. These compounds exhibit good selectivity and cytotoxicity against various proliferative cell lines. The novel compounds disclosed in the aforesaid patent application, have two chiral centers and hence, can exist as four enantiomers i.e. (+)-trans, (−)-trans, (+)-cis and (−)-cis. Chirality has acquired increasing importance for the pharmaceutical industry, as evidenced by the fact that more than 80% of the drugs developed hitherto have chiral properties. The various enantiomers may develop completely different effects in the body, so that only one of two or more enantiomeric forms administered may be effective. In the case of the compounds of Formula 1, it has been observed that only the (+)-trans enantiomers have activity while the (−)-trans enantiomers are inactive. An extensive study by the present inventors of the efficacy of the racemic compounds of Formula 1 and their separate enantiomers has resulted in the applicant's PCT Patent Application No. PCT/IB2006/052002. Administration of the active (+)-trans enantiomer of any of the compounds represented by Formula 1, substantially free of its other isomers, would essentially enable a reduction in the dose of drug. Due to the importance of the (+)-trans enantiomers of the compounds represented by Formula 1 as inhibitors of cyclin dependant kinases, there exists a need to develop an economical and efficient synthetic process for their production.

Applicant's PCT Patent Application No. PCT/IB2006/052002 describes a process for the preparation of the (+)-trans enantiomer of a pyrrolidine substituted with a flavone represented by the following Formula 1;

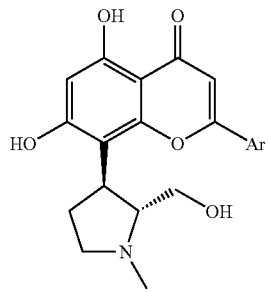

Formula 1 wherein Ar is defined in the detailed description.

The process as described in the PCT Patent Application No. PCT/IB2006/052002 involves resolution of an intermediate compound and subsequent conversion of the resolved intermediate compound to the compound represented by Formula 1. For instance, (+)-trans-2-(2-chlorophenyl)-5,7-dihydroxy-8-(2-hydroxymethyl-1-methyl-pyrrolidin-3-yl)-chromen-4-one was prepared by resolution of an intermediate, namely (±)-trans-[1-methyl-3-(2,4,6-trimethoxy-phenyl)-pyrrolidin-2-yl]-methanol, and subsequent conversion of the (−)-trans isomer of the intermediate to (+)-trans-2-(2-chlorophenyl)-5,7-dihydroxy-8-(2-hydroxymethyl-1-methyl-pyrrolidin-3-yl)-chromen-4-one.

The preparation of the (−)-trans-isomer of the intermediate involves the steps of treating its racemate with a chiral auxiliary to obtain the corresponding (+)- and (−)-trans diastereomeric salts followed by separating the desired diastereomeric salt by crystallization and treating it with a base to yield the desired (−)-trans enantiomer. This resolution method involves significant processing and also the use of resolving agent renders the process costly. Partial recycling of the resolving agent is feasible but such recycling is costly as it requires additional processing and is also associated with waste generation. The undesired enantiomer cannot be recycled and is discarded. The maximum theoretical yield of the key intermediate obtained is just 50% on a laboratory scale synthesis due to loss of half of the racemate. This yield may be further reduced due to the need for high chiral purity (>95% enantiomeric excess). Thus, there is a clear need to develop an alternative asymmetric synthesis which would provide the desired (+)-trans enantiomer in an efficient and more specific manner.

The object of this invention is to provide an alternative process for the preparation of the (+)-trans enantiomer of the compounds represented by Formula 1, which is an enantioselective process. The process of the present invention allows efficient large-scale synthesis by overcoming the drawbacks of the conventional resolution technique.

SUMMARY OF THE INVENTION

The present invention provides a novel process for the enantioselective synthesis of the (+)-trans enantiomer of a compound represented by Formula 1;

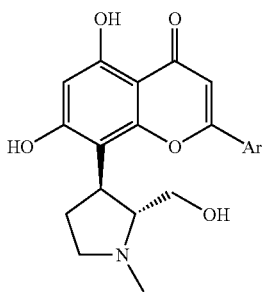

Formula 1 wherein Ar is defined in the detailed description.

The process of the present invention also involves the enantioselective synthesis of a compound of the following Formula A; which is the chiral precursor of the compound of Formula 1;

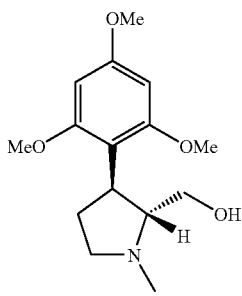

Formula A

The process of the present invention provides an enantioselective synthesis of the (+)-trans enantiomers of the compounds of Formula 1, which avoids the drawbacks of the aforementioned process.

The process of the present invention also has an additional advantage in terms of cost and time as all the intermediates in the process are crystalline and need no further purification.

DETAILED DESCRIPTION OF THE INVENTION

The present invention is specifically directed to a process for the enantioselective synthesis of the (+)-trans enantiomer of a compound represented by Formula 1;

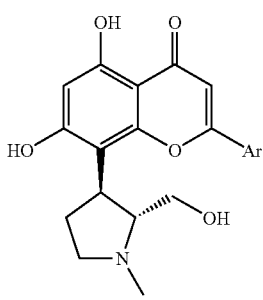

Formula 1 wherein Ar is phenyl, which is unsubstituted or substituted by 1, 2, or 3 identical or different substituents selected from: halogen, nitro, cyano, $C_1$-$C_4$-alkyl, fluoromethyl, difluoromethyl, trifluoromethyl, hydroxyl, $C_1$-$C_4$-alkoxy, carboxy, $C_1$-$C_4$-alkoxycarbonyl, $C_1$-$C_4$-alkylenehydroxyl, $CONH_2$, $CONR_1R_2$, $SO_2NR_1R_2$, cycloalkyl, $NR_1R_2$ and $SR_3$;

wherein $R_1$ and $R_2$ are each independently selected from: hydrogen, $C_1$-$C_4$-alkyl, $C_1$-$C_4$-alkylcarbonyl and aryl, or $R_1$ and $R_2$, together with the nitrogen atom to which they are bonded, form a 5- or 6-membered ring, which may optionally contain at least one additional heteroatom; and $R_3$ is selected from hydrogen, $C_1$-$C_4$-alkyl, aryl and $SR_4$, wherein $R_4$ is $C_1$-$C_4$-alkyl or aryl.

For the purpose of the disclosure, listed below are definitions of various terms used to describe the compounds of the present invention. These definitions apply to the terms as they are used throughout the specification (unless they are otherwise limited in specific instances) either individually or as part of a larger group. They should not be interpreted in the literal sense. They are not general definitions and are relevant only for this application.

The term "alkyl" refers to the radical of saturated aliphatic groups, including straight-chain alkyl groups and branched-chain alkyl groups. Furthermore, unless stated otherwise, the term "alkyl" includes unsubstituted alkyl groups as well as alkyl groups, which are substituted by one or more different substituents. Examples of alkyl residues containing from 1 to 20 carbon atoms are: methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, or t-butyl.

The term "cycloalkyl" refers to a non-aromatic mono or multicyclic ring system of about 3 to 7 carbon atoms which may be unsubstituted or substituted by one or more different substituents. Examples of cycloalkyl groups include cyclopropyl, cyclobutyl, cyclopentyl, cyclohexyl and the like.

The term "alkoxy" as used herein refers to an alkyl group, as defined above, having an oxygen radical attached thereto. Representative alkoxyl groups include methoxy, ethoxy, propoxy, t-butoxy and the like.

The term "halogen" refers to chlorine, bromine, fluorine and iodine.

The term "heteroatom" refers to nitrogen, oxygen, sulphur and phosphorus.

The term "enantiomeric excess" refers to a difference between the amount of one enantiomer and the amount of the other enantiomer that is present in the product mixture. Thus for example, enantiomeric excess of 96% refers to a product mixture having 98% of one enantiomer and 2% of the other enantiomer.

Where the stereochemistry is depicted in the structures it represents a relative rather than an absolute configuration.

In one embodiment of the present invention, there is provided a process for the enantioselective synthesis of the compound, (−)-trans-(1-methyl-3-(2,4,6-trimethoxyphenyl)pyrrolidin-2-yl)methanol represented by the following Formula A;

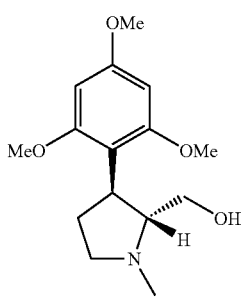

Formula A (hereinafter referred to as compound A), or a pharmaceutically acceptable salt thereof,
which process comprises the steps of:
(a) carrying out a stereospecific Michael addition of dimethyl malonate to (E)-methyl-2-nitro-3-(2,4,6-trimethoxyphenyl)acrylate in a solvent in the presence of a catalyst complex, a base and a molecular sieve, wherein the catalyst complex comprises a chiral bis(oxazoline) ligand and a metal complex, to obtain (+)-trimethyl 3-nitro-2-(2,4,6-trimethoxyphenyl) propane-1,1,3-tricarboxylate represented by the following Formula B;

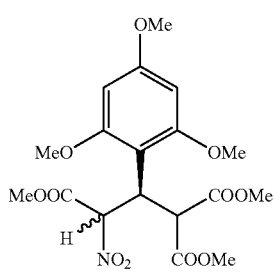

Formula B (hereinafter referred to as compound B);
(b) treating compound B as obtained in step (a) with a reducing agent in a suitable solvent to obtain (+)-dimethyl 5-oxo-3-(2,4,6-trimethoxyphenyl)-pyrrolidine-2,4-dicarboxylate represented by the following Formula C;

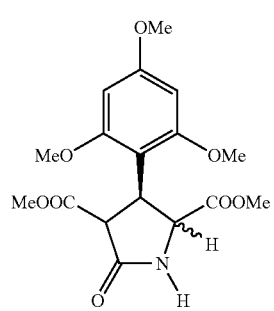

Formula C (hereinafter referred to as compound C);
(c) treating compound C with sodium chloride in a solvent and heating the resulting reaction mixture to a temperature in the range of 120-170° C. to obtain (+)-methyl-5-oxo-3-(2,4,6-trimethoxyphenyl)pyrrolidine-2-carboxylate as a mixture of cis and trans isomers, represented by the following Formula D;

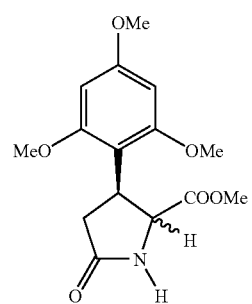

Formula D (hereinafter referred to as compound D);
(d) reacting compound D with a methylating agent and a base selected from: an alkaline metal hydride and an alkaline metal carbonate, in a solvent, followed by subjecting the resulting mixture of cis and trans compounds to alkaline hydrolysis with an alkaline metal hydroxide in an alcohol with heating to a temperature in the range of 50-100° C. to obtain (−)-trans-1-methyl-5-oxo-3-(2,4,6-trimethoxyphenyl)-pyrrolidine-2-carboxylic acid, represented by the following Formula E;

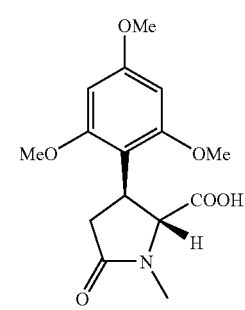

Formula E (hereinafter referred to as compound E) as a single trans isomer;
(e) treating compound E with a reducing agent in a solvent to obtain the desired (−)-trans-(1-methyl-3-(2,4,6-trimethoxyphenyl)pyrrolidin-2-yl)-methanol, represented by Formula A.

In one embodiment, the present invention provides the use of compound A, as obtained by the novel process described, for the preparation of a compound represented by Formula 1.

According to another embodiment of the present invention, there is provided a process for the preparation of the (+)-trans enantiomer of a compound represented by Formula 1;

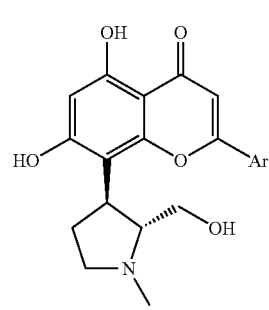

Formula 1 wherein Ar is phenyl, which is unsubstituted or substituted by 1, 2, or 3 identical or different substituents selected from: halogen, nitro, cyano, $C_1$-$C_4$-alkyl, fluoromethyl, difluoromethyl, trifluoromethyl, hydroxyl, $C_1$-$C_4$-alkoxy, carboxy, $C_1$-$C_4$-alkoxycarbonyl, $C_1$-$C_4$-alkylenehydroxyl, $CONH_2$, $CONR_1R_2$, $SO_2NR_1$, $R_2$, cycloalkyl, $NR_1R_2$ and $SR_3$;

wherein $R_1$ and $R_2$ are each independently selected from: hydrogen, $C_1$-$C_4$-alkyl, $C_1$-$C_4$-alkylcarbonyl and aryl, or $R_1$ and $R_2$, together with the nitrogen atom to which they are bonded, form a 5- or 6-membered ring, which may optionally contain at least one additional heteroatom; and $R_3$ is selected from hydrogen, $C_1$-$C_4$-alkyl, aryl and $SR_4$, wherein $R_4$ is $C_1$-$C_4$-alkyl or aryl;

or a pharmaceutically acceptable salt thereof;

which process comprises:

(i) treating compound A (above) with acetic anhydride in the presence of a catalyst to obtain (−)-trans-acetic acid 3-(3-acetyl-2-hydroxy-4,6-dimethoxy-phenyl)-1-methyl-pyrrolidin-2-yl methyl ester represented by the following Formula F;

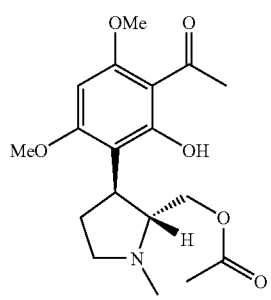

Formula F (hereinafter referred to as compound F);

(ii) treating compound F with an aqueous solution of an alkali and raising the temperature of the reaction mixture to about 50° C. to obtain (−)-trans-1-[2-hydroxy-3-(2-hydroxymethyl-1-methyl-pyrrolidin-3-yl)-4,6-dimethoxy-phenyl)-ethanone represented by the following Formula G;

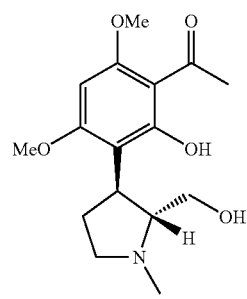

Formula G (hereinafter referred to as compound G);

(iii) reacting compound G with an ester of formula $ArCOOCH_3$ (wherein Ar is as defined in Formula 1) in presence of a base and a suitable solvent under an atmosphere of nitrogen, followed by acid catalyzed cyclisation to give the dimethoxy compound represented by the following Formula 2;

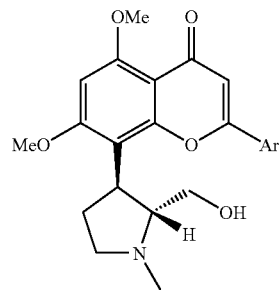

Formula 2

(hereinafter referred to as compound 2);

(iv) subjecting compound 2 to demethylation by heating it with a demethylating agent at a temperature in the range of 120-180° C. to obtain the desired (+)-trans enantiomer of the compound represented by Formula 1.

In the most preferred embodiment, the present invention provides a process for the enantioselective synthesis of (+)-trans-2-(2-chloro-phenyl)-5,7-dihydroxy-8-(2-hydroxymethyl-1-methyl-pyrrolidin-3-yl)-chromen-4-one, represented by the Formula 1A below, where in the compounds of general Formula 1 the Ar group represents phenyl substituted with chlorine;

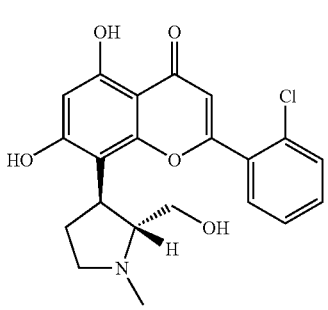

Formula 1A (hereinafter referred to as compound 1A), which process comprises:

(i) treating compound A with acetic anhydride in the presence of a catalyst to obtain (−)-trans-acetic acid 3-(3-acetyl-2-hydroxy-4,6-dimethoxy-phenyl)-1-methyl-pyrrolidin-2-yl methyl ester represented by the following Formula F;

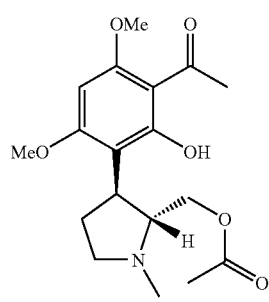

Formula F (hereinafter referred to as compound F);

(ii) treating compound F with an aqueous solution of an alkali and raising the temperature of the reaction mixture to about 50° C. to obtain (−)-trans-1,2-hydroxy-3-(2- hydroxymethyl-1-methyl-pyrrolidin-3-yl)-4,6-dimethoxy-phenyl)-ethanone, represented by the following Formula G;

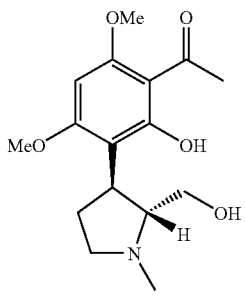

Formula G (hereinafter referred to as compound G);

(iii) reacting compound G with methyl 2-chlorobenzoate in the presence of a base and a suitable solvent under an atmosphere of nitrogen, followed by acid catalysed cyclisation to give (+)-trans-2-(2-chlorophenyl)-8-(2-hydroxymethyl-1-methyl-pyrrolidin-3-yl)-5,7-dimethoxy-chromen-4-one represented by the following Formula 2A;

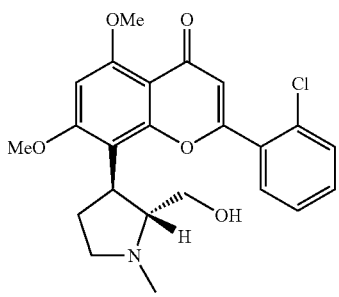

Formula 2A (hereinafter referred to as compound 2A);

(iv) subjecting compound 2A to demethylation by heating it with pyridine hydrochloride at a temperature in the range of 120-180° C. to obtain compound 1A; and (v) optionally, converting compound 1A to its pharmaceutically acceptable salt, such as its hydrochloride salt, (+)-trans-2-(2-chlorophenyl)-5,7-dihydroxy-8-(2-hydroxymethyl-1-methyl-pyrrolidin-3-yl)-chromen-4-one hydrochloride, by conventional means.

The compound (E)-methyl-2-nitro-3-(2,4,6-trimethoxyphenyl)acrylate used in step (a) may be prepared by a reaction between 2,4,6-trimethoxybenzaldehyde and methyl nitroacetate in the presence of ammonium acetate and magnesium sulphate. The compound, 2,4,6-trimethoxybenzaldehyde can be prepared by conventional methods from 2,4,6-trimethoxybenzene by reaction with phosphoryl chloride and N,N-dimethylformamide. The compound methyl nitroacetate can be prepared from nitromethane by conventional methods, for instance, heating nitromethane with a base, for example, potassium hydroxide, at 160° C. followed by treatment at 15° C. with sulphuric acid and methanol.

The catalyst complex used in step (a) above comprises a chiral bis(oxazoline) ligand and a metal complex. The use of chiral bis(oxazoline) ligands in catalytic asymmetric synthesis have been extensively reported (Ghosh, A. K.; Mathivanan, P.; Cappiello, J. *Tetrahedron: Asymmetry* 1998, 9, 1-45). According to the present invention, the preferred chiral bis(oxazoline) ligand is (3aS,3a'S,8aR,8a'R)-2,2'(cyclopropane-1,1-diyl)bis(8,8a-dihydro-3aH-indeno[1,2d]oxazole) which can be prepared as per the method reported in J. Am. Chem. Soc. 2002, 124(44), 13097-13105, which is incorporated herein by reference. The reaction can be carried out using only 4 to 6 mol % chiral bis(oxazoline) ligand.

Metal complexes suitable for providing a catalyst complex include magnesium trifluoromethanesulphonate, magnesium perchlorate, copper trifluoromethanesulphonate, zinc trifluoromethanesulphonate, lanthanum trifluoromethanesulphonate, nickel trifluoromethanesulphonate, magnesium bromide, copper bromide, zinc bromide, nickel bromide, magnesium iodide, copper iodide, zinc iodide, nickel iodide, magnesium acetylacetonate, copper acetylacetonate, zinc acetylacetonate, and nickel acetylacetonate. According to the present invention, the preferred metal complex is magnesium trifluoromethanesulphonate.

The base used in step (a) may be selected from: triethylamine, diisopropylamine, 2,6-lutidine, N-methylmorpholine, N-ethylpiperidine, imidazole and 5,6-dimethylbenzimidazole. Preferably, N-methylmorpholine is used as the base.

The reducing agent as used in step (b) may be stannous chloride or Raney nickel. When stannous chloride is used as the reducing agent, compound C is obtained as a single isomer. When Raney nickel is used as the reducing agent, compound C is obtained as a mixture of isomers, as indicated by $^1$H NMR. If a small sample of the mixture of isomers is purified by column chromatography to separate the isomers, it can be confirmed that one of the isomers is identical to the single isomer obtained using stannous chloride as the reducing agent. The solvent used in step (b) is preferably an aprotic solvent, such as ethyl acetate, dioxane, N,N-dimethylformamide and tetrahydrofuran. When reduction is carried out with stannous chloride, the solvent used is preferably ethyl acetate, and when reduction is carried out with Raney nickel, the solvent used is preferably selected from: tetrahydrofuran, dioxane and N,N-dimethylformamide.

The solvent used in the decarboxylation step (c) is preferably a polar aprotic solvent such as N-methylpyrrolidone and dimethyl sulphoxide.

The methylating agent used in step (d) may be methyl iodide or dimethyl sulphate. The solvent used in step (d) is preferably a polar aprotic solvent which may be selected from: N,N-dimethylformamide, tetrahydrofuran and dioxane. The alkaline metal carbonate may be sodium carbonate or potassium carbonate. The alkaline metal hydride may be sodium hydride. The alkaline metal hydroxide may be sodium hydroxide or potassium hydroxide. The alcohol used is preferably an acyclic alcohol. More preferably, the alcohol is selected from: ethanol, methanol and isopropanol.

The reducing agent used in step (e) is preferably a hydride, more preferably a hydride selected from: lithium aluminium hydride, diisobutyl aluminium hydride and sodium borohydride. The solvent used in the reduction step is preferably an ether. More preferably the solvent is selected from: tetrahydrofuran, dioxane and diethyl ether.

In the process for the preparation of compounds of Formula 1 from the intermediate compounds of Formula A, the catalyst used in step (i) may be selected from a Lewis acid and polyphosphoric acid. The Lewis acid catalyst may be selected from zinc chloride, aluminium chloride, boron trifluoride and boron tribromide. The most preferred Lewis acid catalyst is boron trifluoride.

The alkali used in step (ii) may be sodium hydroxide or potassium hydroxide.

The base used in step (iii) may be selected from: sodium hydride, n-butyl lithium, lithium hexamethyldisilazide and lithium diisopropylamide. The base used is preferably sodium hydride. The solvent used in step (iii) may be selected from: tetrahydrofuran, N,N-dimethylformamide and dioxane. The solvent used is preferably N,N-dimethylformamide.

The demethylating agent used in step (iv) may be selected from pyridine hydrochloride, boron tribromide, boron trifluoride etherate and aluminium trichloride. The preferred demethylating agent is pyridine hydrochloride.

Thus, according to the process of the present invention, the compound of Formula A is obtained with a chiral purity of greater than 97% ee (enantiomeric excess) leading to the compounds of Formula 1 with a chiral purity of greater than 99% ee.

The compounds of Formula 1 obtained by the novel process of the present invention may be optionally converted to their corresponding pharmaceutically or toxicologically acceptable salts, in particular their pharmaceutically utilizable salts.

Compounds of Formula 1 which contain one or more basic groups, i.e. groups which can be protonated can be used according to the invention in the form of their addition salts with non-toxic inorganic or organic acids. Examples of suitable inorganic acids include: boric acid, perchloric acid, hydrochloric acid, hydrobromic acid, sulfuric acid, sulphamic acid, phosphoric acid, nitric acid and other inorganic acids known to the person skilled in the art. Examples of suitable organic acids include: acetic acid, gluconic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulphanilic acid, 2-acetoxybenzoic acid, fumaric acid, toluenesulphonic acid, methanesulphonic acid, ethanedisulphonic acid, oxalic acid, isethionic acid, ketoglutaric acid, benzenesulphonic acid, glycerophosphoric acid and other organic acids known to the person skilled in the art. The compounds of Formula 1, which contain acidic groups can be used according to the invention, for example, as alkali metal salts like Li, Na, and K salts. The pharmaceutically acceptable salts of the present invention can be synthesized from the subject compound, which contains basic and acidic moieties, by conventional chemical methods. Generally, the salts are prepared by contacting the free base or acid with stoichiometric amounts or with an excess of the desired salt-forming inorganic or organic acid or base in a suitable solvent or dispersant or by anion exchange or cation exchange with other salts. Suitable solvents are, for example, ethyl acetate, ether, alcohols, acetone, tetrahydrofuran, dioxane or mixtures of these solvents.

It is understood that modifications in reaction conditions that do not affect the chirality of the various embodiments of this invention are included within the invention disclosed herein. Accordingly, the following examples are intended to illustrate but not to limit the present invention.

EXAMPLES

Example 1

(E)-Methyl-2-nitro-3-(2,4,6-trimethoxyphenyl)acrylate 2,4,6-trimethoxybenzaldehyde (20.75 g, 0.105 mol) was dissolved in dichloromethane (300 mL) and to this solution magnesium sulphate (15 g, 0.124 mol), ammonium acetate (10 g, 0.129 mol) and methyl nitroacetate (12.60 g, 0.105 mol) were added and stirred at room temperature for 2 hours. At the end of two hours, water (300 mL) was added to the reaction mass, the organic layer was separated and the aqueous layer extracted with dichloromethane (2×100 mL). The organic layers were combined and concentrated under reduced pressure to give a solid, which was crystallized from methanol (100 mL).

Yield: 22 g (66.82%) $^1$H NMR (CDCl$_3$): δ 8.37 (s, 1H), 6.08 (s, 2H), 3.86 (s, 3H), 3.84 (s, 3H), 3.82 (s, 6H). MS (ES+): 298 (M+1)

Example 2

(+)-Trimethyl 3-nitro-2-(2,4,6-trimethoxyphenyl)propane-1,1,3-tricarboxylate

In a two-necked 500 mL round-bottomed flask maintained under nitrogen, chloroform (10 mL), magnesium triflate (0.161 g, 0.5 mmol) and water (0.036 mL, 2.0 mmol) were added. To this stirred solution, (3aS,3a'S,8aR,8a'R)-2,2'(cyclopropane-1,1-diyl)bis(8,8a-dihydro-3aH-indeno[1,2-d]oxazole) (bis(oxazoline)) (0.196 g, 0.55 mmol) was added and the reaction mixture stirred for 1 hour. At the end of 1 hour, chloroform (30 mL) and molecular sieves (2 g) were added and the mixture stirred for another 90 mins. (E)-Methyl-2-nitro-3-(2,4,6-trimethoxyphenyl)acrylate (3.1 g, 0.01 mol), dimethyl malonate (1.92 g, 0.014 mol) and N-methylmorpholine (0.06 g, 0.6 mmol) were added and the reaction mixture was stirred for 12 hours followed by heating at 40° C. for 4 hours. Petroleum ether (15 mL) was added to the reaction mixture, stirred for 10 mins. and the mixture filtered. The molecular sieves were washed with methyl-t-butyl ether and the combined organic layer was washed with 5% phosphoric acid (10 mL) and brine (15 mL). The organic layer was concentrated under reduced pressure to give an oil. The oil was dissolved in methanol (10 mL), cooled and filtered to give a white crystalline solid.

Yield: 2.9 g (67.82%) $^1$H NMR (CDCl$_3$): δ (6.05 (br.s, 1H), 6.03 (br.s, 1H), 6.0 (d, 1H, 12.0 Hz), 5.24 (dd, 1H, 9.0 Hz, 12.0 Hz), 4.26 (d, 1H, 9.0 Hz), 3.83 (s, 6H), 3.77 (s, 3H), 3.76 (s, 3H), 3.72 (s, 3H), 3.4 (s, 3H). MS (ES+): 430 (M+1)

Example 3

(+)-Dimethyl 5-oxo-3-(2,4,6-trimethoxyphenyl)pyrrolidine-2,4-dicarboxylate

Method 1

(+)-Trimethyl 3-nitro-2-(2,4,6-trimethoxyphenyl)propane-1,1,3-tricarboxylate (7.8 g, 0.018 mol) was dissolved in ethyl acetate (100 mL). To this solution, stannous chloride dihydrate (25 g, 0.118 mol) was added in portions over a period of 10 mins under stirring. The reaction mixture was heated to 55° C. for 2 hours. The mixture was cooled to 10° C., basified with 10% sodium hydroxide solution to pH 9, filtered through a celite pad and the pad washed with ethyl acetate (50 mL). The aqueous layer was extracted with ethyl acetate (2×100 mL). The organic layers were combined, dried over anhydrous sodium sulphate and concentrated under reduced pressure to give the title compound as a white solid.

Yield: 4.5 g (67.44%) $^1$H NMR (CDCl$_3$): δ 6.06 (br.s, 2H), 6.00 (br.s, 1H), 4.98 (dd, 1H), 4.59 (d, 1H), 3.96 (d, 1H), 3.79 (s, 3H), 3.76 (s, 9H), 3.35 (s, 3H). MS (ES+): 368 (M+1)

Method 2

To a 1 L pressure reactor, tetrahydrofuran (100 mL) and Raney nickel (20 g) was added followed by the addition of a solution of (+)-trimethyl 3-nitro-2-(2,4,6-trimethoxyphenyl) propane-1,1,3-tricarboxylate (32 g, 0.074 mol) in tetrahydrofuran (300 mL). Under stirring, the reactor was purged three times with nitrogen followed by hydrogen. The reaction mixture was stirred overnight under a hydrogen pressure of 80 psi. At the end of the reaction, Raney nickel was filtered off and washed with tetrahydrofuran (150 mL) under nitrogen. The organic layer was concentrated under reduced pressure to yield a white solid. $^1$H NMR revealed the presence of a mixture of isomers. The mixture of cis and trans isomers was obtained in a yield of 25 g (91.32%). A small portion of reaction mixture was purified by column chromatography using 5% methanol in chloroform as eluting agent to separate the isomers and one of the separated isomers was found to be identical to the isomer obtained by reduction using stannous chloride, confirmed by $^1$H NMR, mass spectra and HPLC.

$^1$H NMR (CDCl$_3$): δ 6.06 (br.s, 2H), 6.00 (br.s, 1H), 4.98 (dd, 1H), 4.59 (d, 1H), 3.96 (d, 1H), 3.79 (s, 3H), 3.76 (s, 9H), 3.35 (s, 3H). MS (ES+): 368 (M+1)

Example 4

(+)-Methyl 5-oxo-3-(2,4,6-trimethoxyphenyl)pyrrolidine-2-carboxylate (+)-Dimethyl 5-oxo-3-(2,4,6-trimethoxyphenyl)pyrrolidine-2,4-dicarboxylate (4.0 g, 0.0109 mol) was dissolved in N-methylpyrrolidone (15 mL). Sodium chloride (0.631 g, 0.0109 mol) and water (0.196 mL, 0.0109 mol) were added and the reaction mixture was heated to 170° C. for 5 hours. The reaction mixture was poured on ice (50 g) and the solid was filtered and dried.

Yield: 1.5 g (44.5%)

The product was a mixture of cis and trans isomers as seen in the $^1$H NMR. The mixture of the isomers was used without separation for further reaction. A small amount of the mixture was purified by column chromatography (5% methanol in chloroform) for spectral characterization of the cis and trans isomers.

(+)-cis-Methyl 5-oxo-3-(2,4,6-trimethoxyphenyl) pyrrolidine-2-carboxylate $^1$H NMR (CDCl$_3$): δ 6.08 (s, 2H), 5.89 (br.s, 1H), 4.62 (m, 1H), 4.48 (d, 1H, 9.6 Hz), 3.79 (s, 3H), 3.76 (s, 6H), 3.34 (s, 3H), 2.74 (dd, 1H), 2.60 (dd, 1H). MS (ES+): 310 (M+1)

(+)-trans-Methyl 5-oxo-3-(2,4,6-trimethoxyphenyl) pyrrolidine-2-carboxylate $^1$H NMR (CDCl$_3$): δ 6.15 (s, 2H), 5.87 (br.s, 1H), 4.42 (d, 1H, 7.5 Hz), 4.26 (m, 1H), 3.82 (s, 3H), 3.81 (s, 6H), 3.68 (s, 3H), 2.76 (dd, 1H), 2.53 (dd, 1H). MS (ES+): 310 (M+1)

Example 5

(+)-Methyl-1-methyl-5-oxo-3-(2,4,6 trimethoxyphenyl)pyrrolidine-2-carboxylate (+)-Methyl-5-oxo-3-(2,4,6-trimethoxyphenyl)pyrrolidine-2-carboxylate (1.7 g, 0.0055 mol) was dissolved in N,N-dimethylformamide (15 mL) and the solution cooled to 0° C. Sodium hydride (0.134 g, 0.0056 mmol) was added in portions over a period of 10 minutes and stirred for another 20 minutes at 0° C. Methyl iodide (0.514 mL, 0.0082 mol) was added dropwise and the reaction allowed to warm to room temperature in 1 hour. The reaction mixture was poured slowly over a mixture of crushed ice (20 g) and 1:1 hydrochloric acid solution (5 mL). The mixture was extracted with ethyl acetate (2×50 mL), washed with brine, dried over anhydrous sodium sulphate and concentrated under reduced pressure to yield an oil. The oil was triturated with petroleum ether and the resulting solid was filtered.

Yield: 1.7 g (96.04%)

The product was a mixture of cis and trans isomers as seen in the $^1$H NMR. The mixture of the isomers was used without separation for further reaction. A small amount of the mixture was purified by column chromatography (5% methanol in chloroform) for spectral characterization of the cis and trans isomers.

(+)-cis-methyl 1-methyl-5-oxo-3-(2,4,6-trimethoxyphenyl)pyrrolidine-2-carboxylate $^1$H NMR (CDCl$_3$): δ 6.07 (s, 2H), 4.44 (dd, 1H), 4.27 (d, 1H, 9.6 Hz), 3.79 (s, 3H), 3.74 (s, 6H), 3.38 (s, 3H), 3.20 (dd, 1H), 2.90 (s, 3H), 2.45 (dd, 1H) MS (ES+): 324 (M+1)

(+)-trans-Methyl-1-methyl-5-oxo-3-(2,4,6-trimethoxyphenyl)pyrrolidine-2-carboxylate $^1$H NMR (CDCl$_3$): δ 6.12 (s, 2H), 4.13 (d, 1H, 6.3 Hz), 4.05 (dd, 1H), 3.80 (s, 3H), 3.76 (s, 6H), 3.70 (s, 3H), 2.88 (s, 3H), 2.64 (m, 2H). MS (ES+): 324 (M+1)

Example 6

(−)-trans-1-Methyl-5-oxo-3-(2,4,6-trimethoxyphenyl)pyrrolidine-2-carboxylic acid The mixture of cis and trans isomers of methyl-1-methyl-5-oxo-3-(2,4,6-trimethoxyphenyl)pyrrolidine-2-carboxylate (1.6 g, 0.0049 mol) was dissolved in methanol (15 mL). To this, a solution of potassium hydroxide (0.96 g, 0.017 mol) in water (4 mL) was added and the reaction mixture heated at 65° C. for 3 hours. Methanol was removed under reduced pressure, 15 mL water was added and the mixture acidified with 1:1 hydrochloric acid solution to pH 2. The resulting solid was filtered, washed with water and dried.

Yield: 0.94 g (61.44%) $^1$H NMR (CDCl$_3$): δ 6.13 (s, 2H), 4.16 (m, 2H), 3.80 (S, 3H), 3.77 (S, 6H), 2.93 (S, 3H), 2.74 (m, 1H), 2.62 (m, 1H). MS (ES+); 310 (M+1) $[α]_D^{25}$: −37.83° (c=0.518, MeOH)

Example 7

(−)-trans-(1-methyl-3-(2,4,6-trimethoxyphenyl)pyrrolidin-2-yl)methanol

Lithium aluminum hydride (0.304 g, 0.008 mol) was stirred in tetrahydrofuran (40 mL) under a nitrogen atmosphere. (−)-trans-1-Methyl-5-oxo-3-(2,4,6-trimethoxyphenyl)pyrrolidine-2-carboxylic acid (1.0 g, 0.0032 mol) was added in portions and the reaction mixture was stirred with heating at 50° C. for 90 minutes. The reaction mixture was cooled to 10° C. and diluted with water (2.5 mL) and 15% sodium hydroxide solution (0.6 mL) under stirring. The solid was filtered and washed with ethyl acetate (10 mL). The organic layers were combined and concentrated under reduced pressure to give a white solid.

Yield: 0.91 g (100%) $^1$H NMR (CDCl$_3$): δ 6.16 (s, 2H), 3.98 (m, 1H), 3.64 (s, 9H), 3.62 (dd, 1H), 3.43 (d, 1H), 3.21

(m, 1H), 2.78 (m, 1H), 2.63 (m, 1H), 2.44 (s, 3H), 2.04 (m, 2H) MS (ES+): 282 (M+1) $[\alpha]_D^{25}$: −20° (c=0.2, MeOH)

Example 8

(−)-trans-Acetic acid 3-(3-acetyl-2-hydroxy-4,6-dimethoxy-phenyl)-1-methyl-pyrrolidin-2-yl methyl ester Boron trifluoride diethyl etherate (25.2 g, 0.178 mol) was added dropwise, with stirring, at 0° C., under a nitrogen atmosphere to a solution of (−)-trans-(1-methyl-3-(2,4,6-trimethoxyphenyl)pyrrolidin-2-yl)methanol (10 g, 0.0356 mol) in acetic anhydride (18 g, 0.178 mol). The reaction mixture was stirred at room temperature for 2 h. It was poured over crushed ice (1 kg), basified using a saturated aqueous sodium carbonate solution and extracted using ethyl acetate (3×200 mL). The organic extract was washed with brine, dried (anhydrous sodium sulphate) and concentrated to get title compound.

Yield: 10 g (80%) $^1$H NMR (CDCl$_3$): δ 14.20 (s, 1H), 5.96 (s, 1H), 4.10 (d, 2H), 3.90 (s, 3H), 3.89 (s, 3H), 3.85 (m, 1H), 3.26 (m, 1H), 2.82 (m, 1H), 2.74 (m, 1H), 2.66 (s, 3H), 2.52 (s, 3H), 2.21 (m, 2H), 2.10 (s, 3H).

Example 9

(−)-trans-[2-Hydroxy-3-(2-hydroxymethyl-1-methyl-pyrrolidin-3-yl)-4,6-dimethoxy-phenyl]-ethanone To a solution of (−)-trans-acetic acid-3-(3-acetyl-2-hydroxy-4,6-dimethoxy-phenyl)-1-methyl-pyrrolidin-2-yl methyl ester) (10 g, 0.0284 mol) in methanol (25 mL) was added with stirring, at room temperature, a 10% aqueous sodium hydroxide (25 mL) solution. The temperature of the reaction mixture was raised to 50° C. for 45 minutes, cooled to room temperature, acidified using 1:1 hydrochloric acid solution and concentrated to remove methanol. It was basified using a saturated aqueous sodium carbonate solution. The precipitated compound was filtered, washed with water and dried.

Yield: 7.14 g (81.1%) IR (KBr): 3400, 3121, 3001, 1629, 1590 cm$^{-1}$. $^1$H NMR (CDCl$_3$): δ 5.96 (s, 1H), 3.93 (m, 1H), 3.90 (s 3H), 3.88 (s, 3H), 3.59 (dd, 1H), 3.37 (d, 1H), 3.13 (m, 1H), 2.75 (m, 1H), 2.61 (s, 3H), 2.59 (m, 1H), 2.37 (s, 3H), 2.00 (m, 2H). MS (ES+): m/z 310 (M+1)

Example 10

(+)-trans-2-(2-Chlorophenyl)-8-(2-hydroxymethyl-1-methyl-pyrrolidin-3-yl)-5,7-dimethoxy-chromen-4-one Sodium hydride (50%, 0.54 g, 0.01125 mol) was added in portions to a solution of (−)-trans-acetic acid 3-(3-acetyl-2-hydroxy-4,6-dimethoxy-phenyl)-1-methyl-pyrrolidin-2-yl methyl ester (0.7 g, 0.0022 mol) in N,N-dimethylformamide (15 mL) at 0° C., under a nitrogen atmosphere and with stirring. After 10 minutes, methyl 2-chlorobenzoate (1.15 g, 0.00675 mol) was added. The reaction mixture was stirred at 25° C. for 2 h. Methanol was added carefully below 20° C. The reaction mixture was poured over crushed ice (300 g), acidified with 1:1 hydrochloric acid solution to pH 2 and extracted using ethyl acetate (2×100 mL). The aqueous layer was basified using a saturated sodium carbonate solution to pH 10 and extracted using chloroform (3×200 mL). The organic layer was dried over anhydrous sodium sulphate and concentrated. To the residue, concentrated hydrochloric acid (25 mL) was added and stirred at room temperature for 2 h. The reaction mixture was poured over crushed ice (300 g) and made basic using a saturated sodium carbonate solution. The mixture was extracted using chloroform (3×200 mL). The organic extract was washed with water, dried over anhydrous sodium sulphate and concentrated to obtain the title compound.

Yield: 0.67 g (68.88%) mp: 95-97° C. IR (KBr): 3400, 1660 cm$^{-1}$. $[\alpha]_D^{25}$=+5.8° (c=0.7, methanol) $^1$H NMR (CDCl$_3$): δ 7.7 (dd, 1H), 7.41 (m, 1H), 7.45 (m, 2H), 6.55 (s, 1H), 6.45 (s, 1H), 4.17 (m, 1H), 4.05 (s, 3H), 3.95 (s, 3H), 3.65 (dd, 1H), 3.37 (dd, 1H), 3.15 (m, 1H), 2.77 (d, 1H), 2.5 (m, 1H), 2.3 (s, 3H), 2.05 (m, 2H). MS: m/e 430 (M$^+$), 398 (M−31)

Example 11

(+)-trans-2-(2-Chlorophenyl)-8-(2-hydroxymethyl-1-methyl-pyrrolidin-3-yl)-5,7-dihydroxy-chromen-4-one Molten pyridine hydrochloride (4.1 g, 0.0354 mol) was added to (+)-trans-2-(2-chlorophenyl)-8-(2-hydroxymethyl-1-methyl-pyrrolidin-3-yl)-5,7-dimethoxy-chromen-4-one (0.4 g, 0.0009 mol) and heated at 180° C. for 1.5 h. The reaction mixture was cooled to 25° C., diluted with methanol (10 mL) and basified using sodium carbonate to pH 10. The mixture was filtered and the organic layer was concentrated. The residue was suspended in water (5 mL), stirred for 30 minutes, filtered and dried to obtain the title compound.

Yield: 0.25 g (66.86%) IR (KBr): 3422, 3135, 1664, 1623, 1559 cm$^{-1}$. $^1$H NMR (CDCl$_3$): δ 7.56 (d, 1H), 7.36 (m, 3H), 6.36 (s, 1H), 6.20 (s, 1H), 4.02 (m, 1H), 3.70 (m, 2H), 3.15 (m, 2H), 2.88 (m, 1H), 2.58 (s, 3H), 2.35 (m, 1H), 1.88 (m, 1H). MS (ES+): m/z 402 (M+1) Analysis: $C_{21}H_{20}ClNO_5$ C, 62.24 (62.71); H, 5.07 (4.97); N, 3.60 (3.48); Cl, 9.01 (8.83).

Example 12

(+)-trans-2-(2-Chloro-phenyl)-5,7-dihydroxy-8-(2-hydroxymethyl-1-methyl-pyrrolidin-3-yl)-chromen-4-one hydrochloride (+)-trans-2-(2-Chlorophenyl)-8-(2-hydroxymethyl-1-methyl-pyrrolidin-3-yl)-5,7-dimethoxy-chromen-4-one (0.2 g, 0.48 mmol) was suspended in methanol (2 mL) and ethereal HCl (5 mL) was added. The suspension was stirred to get a clear solution. The solution was concentrated under reduced pressure to obtain the title compound.

Yield: 0.21 g (97%) $[\alpha]_D^{25}$=+21.2° (c=0.2, methanol) $^1$H NMR (CD$_3$OD, 300 MHz): δ 7.80 (d, 1H), 7.60 (m, 3H), 6.53 (s, 1H), 6.37 (s, 1H), 4.23 (m, 1H), 3.89 (m, 2H), 3.63 (m, 1H), 3.59 (dd, 1H), 3.38 (m, 1H), 2.90 (s, 3H), 2.45 (m, 1H), 2.35 (m, 1H). MS (ES+): m/z 402 (M+1), free base.

What is claimed is:

1. A process for the preparation of the compound (−)-trans-(1-methyl-3-(2,4,6-trimethoxyphenyl)pyrrolidin-2-yl)-methanol represented by Formula A;

Formula A

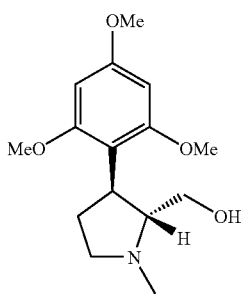

comprising treating the compound (−)-trans-1-methyl-5-oxo-3-(2,4,6-trimethoxyphenyl)pyrrolidine-2-carboxylic acid of the following Formula E;

Formula E

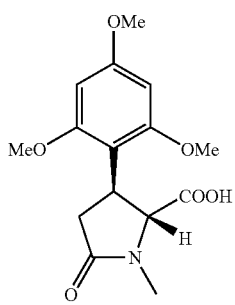

(hereinafter referred to as compound E), with a reducing agent in a solvent.

2. The process according to claim 1, wherein the reducing agent is a hydride.

3. The process according to claim 2, wherein the hydride is selected from lithium aluminium hydride, diisobutyl aluminium hydride and sodium borohydride.

4. The process according to claim 1, wherein the solvent used is an ether.

5. The process according to claim 4, wherein the ether is selected from tetrahydrofuran, dioxane and diethyl ether.

6. The process according to claim 1, wherein the compound E is prepared by (a) carrying out a stereospecific Michael addition of dimethyl malonate to (E)-methyl-2-nitro-3-(2,4,6-trimethoxyphenyl)acrylate in a solvent in the presence of a catalyst complex, a base and molecular sieves, wherein the catalyst complex comprises a chiral bis(oxazoline) ligand and a metal complex, to obtain (+)-trimethyl-3-nitro-2-(2,4,6-trimethoxyphenyl) propane-1,1,3-tricarboxylate represented by the following Formula B;

Formula B

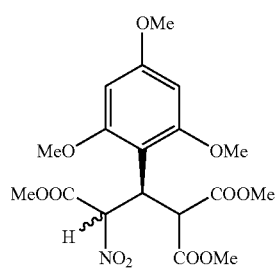

(hereinafter referred to as compound B);

(b) treating compound B as obtained in step (a) with a reducing agent in a solvent to obtain (+)-dimethyl-5-oxo-3-(2,4,6-trimethoxyphenyl)-pyrrolidine-2,4-dicarboxylate represented by the following Formula C;

Formula C

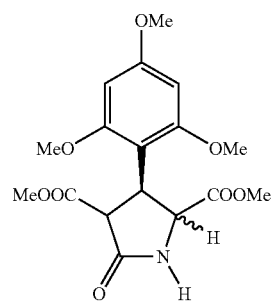

(hereinafter referred to as compound C);

(c) treating compound C with sodium chloride in a solvent and heating the resulting reaction mixture to a temperature in the range of 120° C. to 170° C. to obtain (+)-methyl-5-oxo-3-(2,4,6-trimethoxyphenyl)pyrrolidine-2-carboxylate as a mixture of cis and trans isomers, represented by the following Formula D;

Formula D

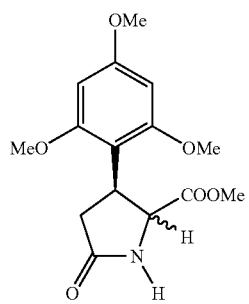

(hereinafter referred to as compound D);

(d) reacting compound D with a methylating agent in a solvent and a base selected from an alkaline metal hydride and an alkaline metal carbonate; followed by subjecting the resulting mixture of cis and trans compounds to alkaline hydrolysis with an alkaline metal hydroxide in an alcohol, and heating the resulting reaction mixture to a temperature in the range of 50° C. to 100° C. to obtain compound E as a single trans isomer.

7. The process according to claim 6, wherein the chiral bis(oxazoline) ligand used in step (a) is (3aS,3a'S,8aR,8a'R)-2,2'(cyclopropane-1,1-diyl)bis(8,8a-dihydro-3aH-indeno[1,2d]oxazole).

8. The process according to claim 6, wherein the metal complex used in step (a) is selected from magnesium trifluoromethanesulphonate, magnesium perchlorate, copper trifluoromethanesulphonate, zinc trifluoromethanesulphonate, lanthanum trifluoromethanesulphonate, nickel trifluoromethanesulphonate, magnesium bromide, copper bromide, zinc bromide, nickel bromide, magnesium iodide, copper iodide, zinc iodide, nickel iodide, magnesium acetylacetonate, copper acetylacetonate, zinc acetylacetonate, and nickel acetylacetonate.

9. The process according to claim 8, wherein the metal complex is magnesium trifluoromethanesulphonate.

10. The process according to claim 6, wherein the base used in step (a) is selected from triethylamine, diisopropylamine, 2,6-lutidine, N-methylmorpholine, N-ethylpiperidine, imidazole and 5,6-dimethylbenzimidazole.

11. The process according to claim 10, wherein the base is N-methylmorpholine.

12. The process according to claim 6, wherein in step (b), the treatment of compound B with a reducing agent in a solvent is carried out using stannous chloride as the reducing agent.

13. The process according to claim 12, wherein the solvent is ethyl acetate.

14. The process according to claim 6, wherein in step (b), the treatment of compound B with a reducing agent in a solvent is carried out using Raney nickel as the reducing agent.

15. The process according to claim 14, wherein the solvent is selected from tetrahydrofuran, dioxane and N,N-dimethylformamide.

* * * * *